United States Patent [19]
McKay et al.

[11] Patent Number: 4,459,985
[45] Date of Patent: Jul. 17, 1984

[54] TIBIAL PROSTHESIS EXTRACTOR AND METHOD FOR EXTRACTING A TIBIAL IMPLANT

[75] Inventors: William F. McKay, Towaco; Peter B. Van Syckle, Rutherford, both of N.J.

[73] Assignee: Howmedica Inc., New York, N.Y.

[21] Appl. No.: 472,335

[22] Filed: Mar. 4, 1983

[51] Int. Cl.³ .................. A61B 17/00; A61B 17/18
[52] U.S. Cl. .................. 128/303 R; 3/1.911; 128/92 EC
[58] Field of Search .......... 128/303 R, 92 EC, 92 E, 128/92 C, 83; 3/1.911, 1.91

[56] References Cited

U.S. PATENT DOCUMENTS

| 4,151,838 | 5/1979 | Crew | 128/303 R X |
| 4,209,861 | 7/1980 | Walker et al. | 3/1.911 |
| 4,222,382 | 9/1980 | Antonsson et al. | 128/303 R |
| 4,274,163 | 6/1981 | Malcom et al. | 3/1.911 X |

FOREIGN PATENT DOCUMENTS

| 761910 | 1/1954 | Fed. Rep. of Germany | 128/92 EC |
| 700119 | 11/1979 | U.S.S.R. | 128/303 R |

Primary Examiner—Ronald L. Frinks
Attorney, Agent, or Firm—Charles J. Knuth; Peter C. Richardson

[57] ABSTRACT

An extractor for dislodging an implanted tibial prosthesis comprising substantially parallel upper and lower members joined by a yoke, with the lower member comprising a pair of forked blades to insert under the tibial component and the upper member being adapted to receive means for applying upward dislodging force.

5 Claims, 4 Drawing Figures

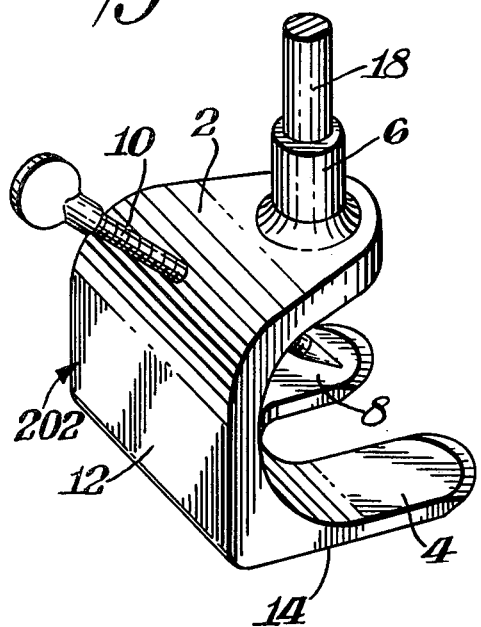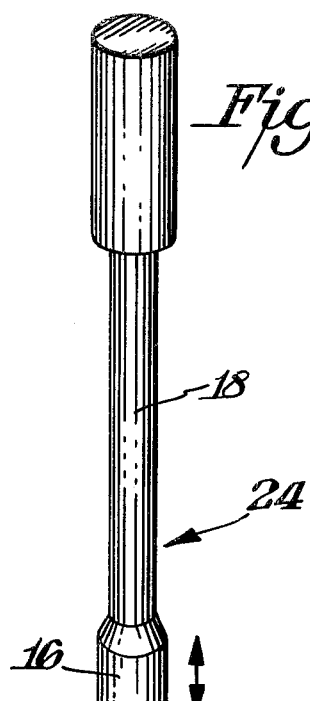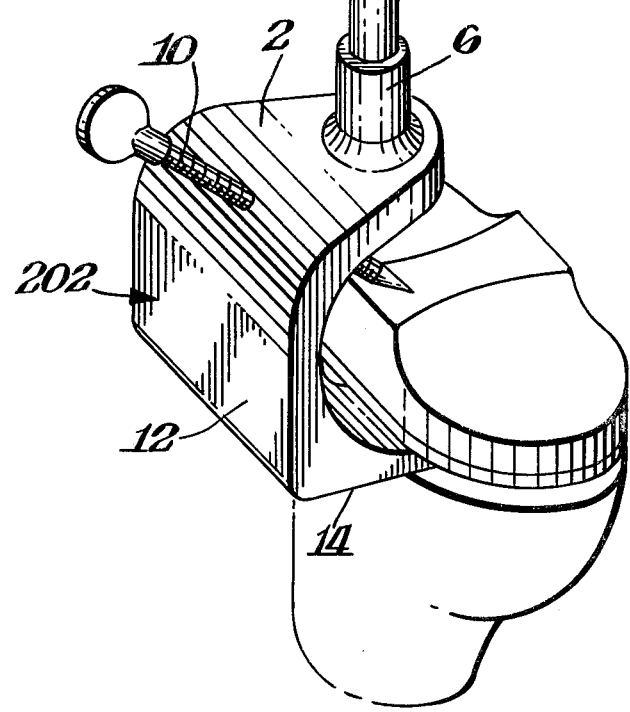

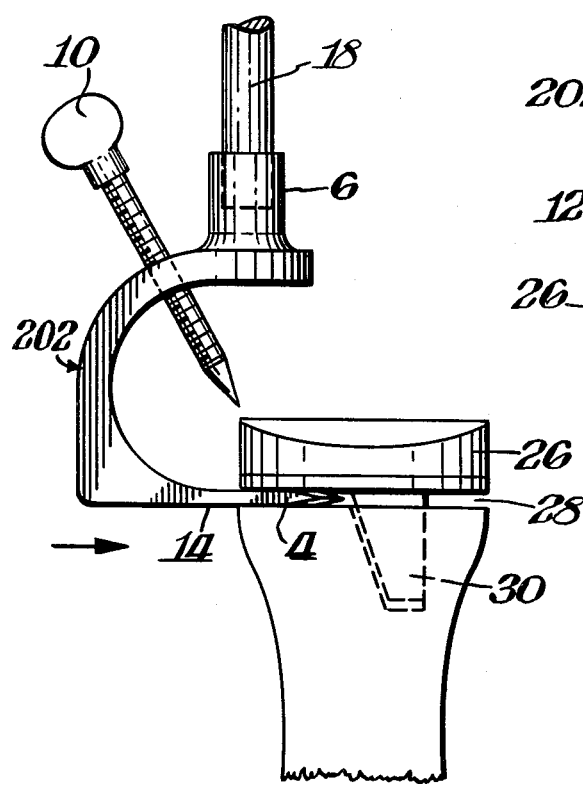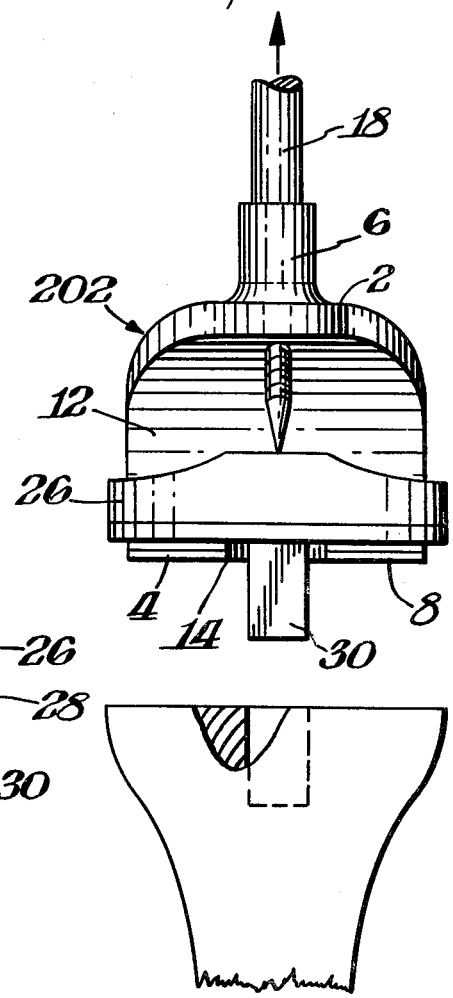

TIBIAL PROSTHESIS EXTRACTOR AND METHOD FOR EXTRACTING A TIBIAL IMPLANT

BACKGROUND OF THE INVENTION

The present invention concerns a novel extractor for removing an implanted tibial prosthesis, and in particular removal of tibial trays from the proximal tibia during surgical revision.

Current methods used to remove tibial prostheses include using an osteotome as a lever by prying under the edge of the tibial tray. This often leads to chipping and cracking of the bone stock under the tray. Accordingly, there has been a need for a device to remove an implanted tibial prosthesis that does not result in these undesired effects.

SUMMARY OF THE INVENTION

The main object of the present invention is to provide an extractor for dislodging an implanted tibial prosthesis having a tibial tray and stem, comprising substantially parallel upper and lower members joined by a yoke at one end; the members are sufficiently spaced by the yoke to admit the tibial tray there between; the lower member comprises a pair of forked blades for insertion between the tibial tray and the proximal end of the tibia, straddling the tibial stem; the upper member is adapted to receive means for applying upward dislodging force to the tibial tray in a substantially axial alignment with the tibial stem to extract the prosthesis from the tibia. The upper member is adapted to attach means for applying such dislodging force.

The extractor is preferably provided with anchoring means for fixed securement to the tibial tray while the dislodging force is applied. Preferably, the anchoring means is a pointed screw threaded therethrough for engaging a plastic insert in the tibial tray.

The invention also embraces a method of extracting the tibial implant having a tibial tray and stem comprising the steps of excising a layer of proximal tibial bone, inserting forked means into the space created between the tray and proximal tibial surface, straddling the stem, and transmitting a dislodging force to the tray through the forked member in a direction substantially coaxial with the stem.

BRIEF DESCRIPTION OF THE DRAWINGS

Novel features and advantages of the present invention, in addition to those mentioned above, will become apparent from a reading of the following detailed description in conjunction with the accompanying drawings, wherein:

FIG. 1 is an isometric view of a prosthesis extractor of the present invention.

FIG. 2 is an isometric view of the extractor that includes means to apply force to dislodge the prosthesis.

FIG. 3 is a side elevational view of the extractor.

FIG. 4 is a front elevational view of the extractor with the prosthesis removed.

DESCRIPTION OF THE PREFERRED EMBODIMENT

A preferred embodiment of the extractor 202 of the present invention is shown in FIG. 1 and comprises substantially paralled upper and lower members 2 and 14, respectively connected by a yoke 12. The lower member 14 has a pair of forked blades 4 and 8, which are adapted for insertion between the tibial tray and the proximal end of the tibia, straddling the tibial stem. The upper member 2 is adapted to receive means for applying upward dislodging force to the prosthesis. In FIG. 1 6 is an internally threaded well into which a male threaded means may be inserted to apply said dislodging force. Preferably, the extractor has anchoring means 10 for fixedly securing the extractor to the tibial tray while the dislodging force is applied. The anchoring means 10 is, for example, a pointed screw threaded therethrough for engaging a plastic insert on the tibial tray.

FIG. 2 shows the extractor 202 together with means 24 for applying the upward dislodging force which is screwed into threaded well 6. The dislodging force is applied by moving a sliding weight 16 upwards along shaft 18, thereby transmitting an impact shock to the tibial tray which dislodges the implanted prostheses. By employing the extractor of the present invention the dislodging force is applied in substantially axial alignment with the tibial stem, thereby most effectively breaking the cement bond between the prosthesis and the bone.

FIGS. 3 and 4 illustrate the manner in which the extractor 202 is employed to remove a tibial prosthesis. Referring to FIG. 3, a layer of proximal tibial bone immediately below the tibial tray 26 is excised to create a space 28 into which the blades 4 and 8 are inserted so as to straddle the tibial stem 30. The threaded screw 10 is tightened against the tibial tray 26. Upward dislodging force is applied to the upper member to break the cement bond between the tibial tray and the proximal bone, thereby removing the tibial prosthesis as illustrated by; FIG. 4.

The prosthesis extractor 202 eliminates many of the problems of previously used removal techniques and provides a relatively simple system, yet one that applies the necessary impact force to dislodge such prosthesis without damage to the bone.

It is a relatively uncomplicated design, offers easy manipulation and sterilization and is adapted for use with existing impact-providing devices.

Further modifications of the invention disclosed herein will occur to persons skilled in the art and the invention is not limited to the specific embodiments described in the specification. Rather, the scope of the present invention is limited only by the appended claims.

We claim:

1. An extractor for dislodging an implanted tibial prosthesis having a tibial tray and stem,
    said device comprising substantially parallel upper and lower member joined by a yoke at one end thereof,
    said members being sufficiently spaced by said yoke to admit said tibial tray therebetween,
    said lower member comprising a pair of forked blades for insertion between said tray and the proximal end of the tibia, straddling said stem,
    and said upper member being adapted to receive means for applying upward dislodging force to said tray in substantially axial alignment with said stem to extract said prosthesis from said tibia.

2. The extractor of claim 1 wherein said upper member is adapted to attach an impact device thereto for applying said dislodging force.

3. The extractor of claim 1 having anchoring means for fixed securement to said tibial tray while said dislodging force is applied.

4. The extractor of claim 3 wherein said anchoring means is a pointed screw threaded therethrough for engaging a plastic insert in said tibial tray.

5. A method for extracting a tibial implant having a tibial tray and stem comprising excising a layer of proximal tibial bone immediately below said tibial tray, inserting fork means into the space so created between the tray and the proximal tibia surface, straddling said stem, and transmitting impact shock to said tray through said fork means in a direction substantially coaxial with said stem.

* * * * *